(12) United States Patent
Löhr et al.

(10) Patent No.: US 7,083,607 B2
(45) Date of Patent: Aug. 1, 2006

(54) INJECTION DEVICE AND METHOD FOR INJECTING CAPSULES

(75) Inventors: Matthias Löhr, Weinheim (DE); Walter Günzburg, Mödling (AT)

(73) Assignee: Bavarian Nordic A/S, Kvistgaard (DK)

( * ) Notice: Subject to any disclaimer, the term of this patent is extended or adjusted under 35 U.S.C. 154(b) by 0 days.

(21) Appl. No.: 10/483,711

(22) PCT Filed: Jul. 12, 2002

(86) PCT No.: PCT/EP02/07803

§ 371 (c)(1),
(2), (4) Date: Feb. 19, 2004

(87) PCT Pub. No.: WO03/005913

PCT Pub. Date: Jan. 23, 2003

(65) Prior Publication Data

US 2004/0199120 A1    Oct. 7, 2004

(30) Foreign Application Priority Data

Jul. 12, 2001    (DK) ................. 2001 01094

(51) Int. Cl.
*A61M 31/00*    (2006.01)

(52) U.S. Cl. ........................... 604/506; 604/60

(58) Field of Classification Search .......... 604/57, 604/59, 60, 61, 63, 164.01, 164.06, 164.07, 604/164.09–164.11, 187, 199, 239, 272, 274; 600/1, 3, 4, 7, 8

See application file for complete search history.

(56) References Cited

U.S. PATENT DOCUMENTS

| | | | | |
|---|---|---|---|---|
| 4,755,175 A | * | 7/1988 | Nilsson | 604/268 |
| 5,496,332 A | * | 3/1996 | Sierra et al. | 606/139 |
| 6,162,203 A | * | 12/2000 | Haaga | 604/272 |
| 2002/0143387 A1 | * | 10/2002 | Soetikno et al. | 623/1.15 |

* cited by examiner

*Primary Examiner*—LoAn H. Thanh
(74) *Attorney, Agent, or Firm*—Andrew Wilford

(57) ABSTRACT

The invention relates to an injection device containing a hollow needle (1), a cutting needle that can be inserted into the hollow needle and that has a cutting tip projecting from the front end of the hollow needle, a catheter (9) that replaces said cutting needle and that can be inserted approximately up to its front end into the hollow needle (9), said catheter having a receiving chamber (30) for a substance in the form of a capsule on its distal end, in addition to a mandrin (29) that can be inserted into the catheter (9) and which can be placed in a position defining a receiving chamber (30) filled with capsules (22) on the distal end of said catheter, wherein the capsules (22) contained in the receiving chamber (30) of the inserted catheter (9) are released without exerting any pressure in the target area of the body (23) once the injection device has been arranged in a target area of a body (23) by relatively pulling back both the catheter (9) and the hollow needle (1) in relation to the mandrin (29) and by then withdrawing the mandrin (29). Preferably, the catheter (9) contains a removable sieve (28) on its frond end.

12 Claims, 3 Drawing Sheets

INJECTION DEVICE AND METHOD FOR INJECTING CAPSULES

CROSS REFERENCE TO RELATED APPLICATION

This application is a national stage of PCT/EP02/07803 filed 12 Jul. 2002 and based upon Denmark National Application PA 2001 01094 filed 12 Jul. 2001 under the International Convention.

FIELD OF THE INVENTION

The invention relates to an injection device for introducing capsules into a body and a method for introducing capsules containing a substance into a body by means of an injection device.

BACKGROUND OF THE INVENTION

For introducing a liquid medicament into a patient's body catheter/needle assemblies have been used. U.S. Pat. No. 5,470,318 discloses such an assembly including a hollow needle for puncturing a region of interest in the body. A flexible tube is inserted through the hollow needle and a liquid medicament is introduced through the tube into the body. Medicaments which are contained in pressure sensitive capsules can not be delivered by means of such an injection device because the capsules would break and would be destroyed because of the pressure exerted on them while they are injected.

OBJECT OF THE INVENTION

The object of the present invention is to devise an initially mentioned type of injection device which can also be used to deliver substances or cells in the form of pressure sensitive capsules and to devise such a method.

SUMMARY OF THE INVENTION

This object is achieved in accordance with the present invention by an injection device.

Comprising:

a hollow needle, a cutting needle insertable in the hollow needle and slidable therein with a cutting tip protruding from the front or distal end of the hollow needle, and a catheter for replacing the cutting needle in the hollow needle. The catheter is slidable approximately up to the front end of the hollow needle and has at its distal end a reservoir for a substance in the form of capsules; and A mandrin which can be inserted into the catheter and which can be placed therein in a position in which it defines the reservoir filled with capsules on the distal end of the catheter;

The capsules contained in the reservoir of the inserted catheter are released largely without exerting any pressure in the target area of the body once the injection device has been arranged in a target area of a body by relatively withdrawing both the catheter and the hollow needle in relation to the mandrin followed by with-drawing the mandrin from the body. The catheter can contain a detachable sieve on its front end.

Using the hollow needle and the cutting needle which is inserted in the hollow needle and positioned therein in such a position that its cutting tip extends beyond the distal end of the hollow needle the point of interest in the body, for example in a tumor, or in general in a living organism is punctuated. The cutting needle is subsequently removed from the hollow needle which is held stationary and replaced by the catheter which is inserted into the hollow needle and is pushed forward until reaching the front end of the hollow needle. The catheter includes at its front or distal end a reservoir or cavity for the substance or a medicament which is present in the form of capsules. The mandrin can be inserted in the catheter and, by being pushed forward, can be arranged in a predetermined position in which the mandrin, at least with its front side, borders the reservoir from its back side. By inserting the catheter to which the mandrin is fixedly connected into the hollow needle the capsules will be brought into the body's region where they are to be delivered. As the capsules are enclosed by the catheter pressure can not be exerted on them. Then, the unit composed of the hollow needle and the catheter is withdrawn from the mandrin being held stationary and in this way the outer cover of the reservoir is removed. Dependent on the configuration of the mandrin, either by withdrawing the outer cover and/or by subsequently withdrawing the mandrin with the hollow needle and the catheter in simultaneous movement the capsules will be left in the puncture channel formed by the hollow needle in the body. Thus, using the injection device according to the invention the capsules are not injected by pressure into the body but they are brought into the target area while they are protected in the reservoir in the catheter and, after removing the cover, they are released in the puncture channel largely without pressure acting on them, If the hollow needle is held in the target area in the body while the catheter is retracted another catheter loaded with capsules can be inserted within the hollow needle and the capsules can be delivered into the body in the same way as described. Thus the injection device is suited for multiple injection at the same position or in an adjacent area of the body.

Instead of introducing a substance or a medicament the injection device generally may be used for delivering cells, microspheres, lipid bodies, fullerenes and such which are present in the form of capsules or similar pressure sensitive carrier means into a body. The term "body" comprehends human or animal bodies, parts of bodies or other bodies into which the injection device may penetrate in a cutting manner because of the structure of these bodies. These bodies comprise for example plants, animal or vegetable products in particular in the food sector or other technical products or objects into which substances or agents are to be de-livered for effecting reactions. The capsules or carrier means are formed for example such that the substances or agents contained therein can be released slowly into the body.

Preferably, the catheter contains on its front end a removable sieve which during loading of the catheter with capsules allows for rinsing of the taken up capsules with a rinsing liquid, in particular a physiological saline, which can drop off through the sieve. This sieve has to be removed from the catheter before the capsules will be delivered from the reservoir of the catheter into the body. For achieving this, provisions can be made so that a front section of the catheter containing the sieve can be separated or broken off at a predetermined breaking point where the strength of the catheter forming material is weakened. Just before inserting the catheter into the hollow needle the front section holding the sieve has to be broken off. In an alternative embodiment the mandrin comprises at its front section an extension which extends along the reservoir and which includes a cutting de-vice for separating the sieve from the catheter so that the sieve remains in the body. If necessary the sieve can be made of a decomposing material and in particular it is biologically degradable. While the catheter is displaced relative to the mandrin the cutting device cuts off the sieve which remains in the body. The extension may be provided, e.g., in the form of at least two pin-like projecting parts which project from the front end of the mandrin and which carry at least two cutting teeth or a cutting ring.

Preferably, the mandrin includes in its front section a cavity open to the distal end 30 and forming the reservoir and a front end forming a circular cutting edge. Thus, the reservoir is not directly formed by the catheter but from the wall surrounding the cavity of the mandrin. In order to support and to ease the free movement of the capsules out of the mandrin the cavity or the reservoir has a cross-section which widens in the direction from its interior to the open end.

Preferably, the mandrin is formed in such a way that it can be arranged easily on the catheter in a first position in which the mandrin's front end is retracted from the front end of the catheter for delimiting the reservoir, and in a second position in which the mandrin's front end stays flush with the front end of the catheter. In order to ease the process of positioning the mandrin may have a marking or markings. Furthermore, a mandrin stopper may be provided for optionally setting a limitation for the mandrin's movement relative to the catheter.

In the method aspect of the invention the front or distal end of a hollow needle of the injection device is positioned in a target area in the body, subsequently a catheter is inserted in the hollow needle the catheter having at its distal end a reservoir or receiving chamber filled with capsules and a mandrin delimiting the reservoir. Then, the catheter and the hollow needle are both withdrawn relative to the mandrin being held stationary whereby the capsules are delivered in the target area of the body largely without exerting any pressure, and afterwards the mandrin is withdrawn from the body.

Preferably a sieve which is provided on the front end of the catheter and which delimits the reservoir distally is cut off from the catheter by means of the mandrin while the catheter is retracted relative to the mandrin and the capsules are re-leased without exerting any pressure while the catheter and the hollow needle or alternatively the catheter, the hollow needle and the mandrin are retracted.

Advantageously the catheter and the hollow needle are withdrawn from the mandrin being held stationary approximately over the length of the reservoir and after releasing the capsules the catheter and the mandrin are completely withdrawn and the hollow needle is be pushed forward in the target area for capsules to be delivered once more. Then another catheter which is filled with capsules and contains another mandrin is pushed forward into the hollow needle, whereupon the capsules again are released in the body in the manner as described without exerting any pressure.

This method has the advantage that the capsules can be filled into the reservoir largely without exerting any pressure, in particular by means of a syringe.

BRIEF DESCRIPTION OF THE DRAWING

Preferred embodiments of the injection device are explained in the following with reference to the drawings wherein.

SPECIFIC DESCRIPTION

Figure 1:
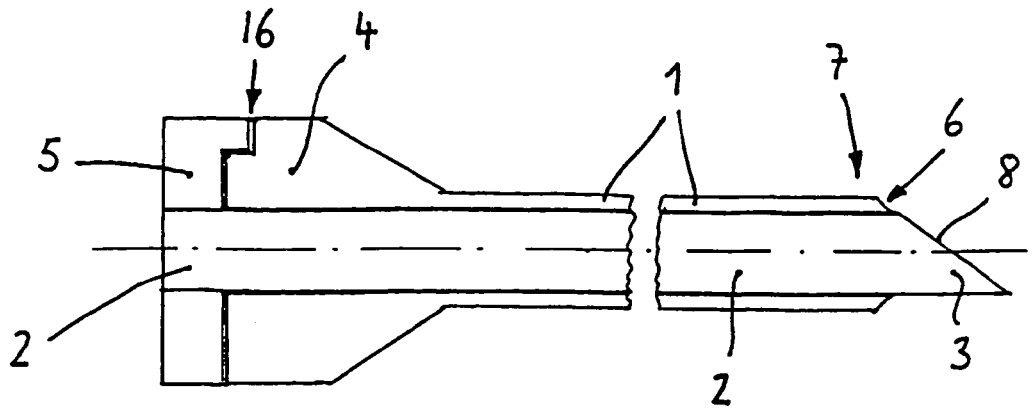
FIG. 1 is a lengthwise section through an injection device having a hollow needle and a cutting needle.

Referring to FIG. 1 an injection device comprises an outer hollow needle 1 and a cutting needle 2, which is inserted into the hollow needle 1 with zero backlash and which is axially displaceable therein. The cutting needle 2 has an atraumatic formed cutting tip 3. The hollow needle 1 and the cutting needle 2 are provided with attachments 4 and 5, respectively, at their respective back or proximal ends. The attachments 4 and 5 constitute a connecting or interlocking means, e.g., a Luer lock connection, and also a handle for releasably joining or interlocking the cutting needle 2 with the hollow needle 1 so that the cutting needle 2 can be locked with the hollow needle 1, e.g., in the position shown in FIG. 1, in which the cutting tip 3 extends a small distance, e.g., 5 mm, beyond the front end 7 of the hollow needle 1. The front end 7 of hollow needle 1 has a circumferential bevelling 6 so that the sharpened bevelling 8 of the cutting tip 3 changes almost continuously into the circumferential bevelling 6 of the hollow needle 1.

Figure 2:
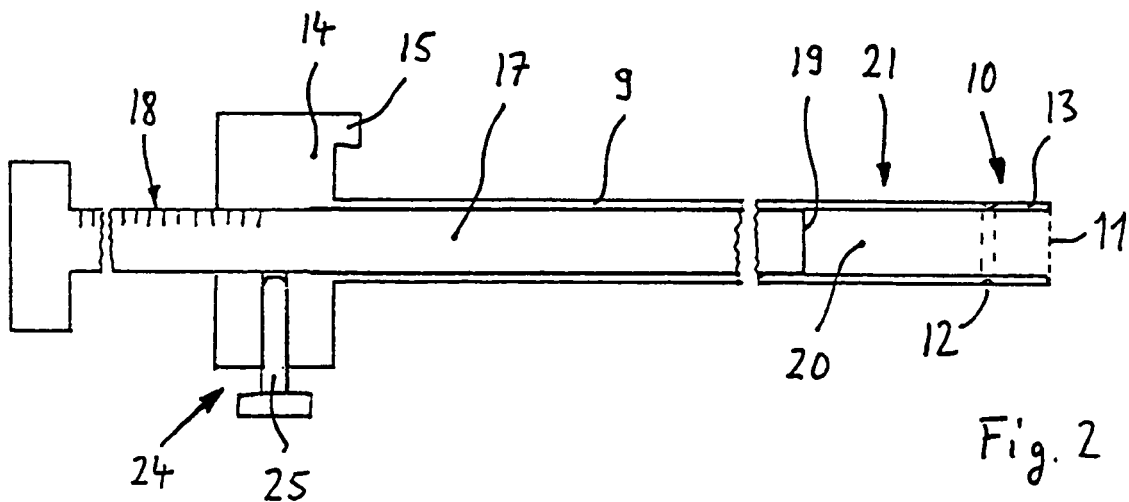
FIG. 2 is a lengthwise section through a catheter of the injection device and a mandrin inserted in the catheter.

The injection device further comprises a loading device including a catheter 9 (FIG. 2) for replacing the cutting needle 2 in its position within the hollow needle 1 which catheter 9 can be inserted into the hollow needle 1 matching therein with zero backlash. The catheter 9 comprises at its front end 10 a sieve 11 with a mesh size of, e.g., 0.1 mm and a predetermined breaking point or line 12 arranged slightly backwards from the sieve 11 and being formed, e.g., as a pre-made rim or circumferential groove of minimal breaking resistance so that the sieve 11 is removable from the catheter 9 by breaking away the sieve carrying part 13 at the predetermined breaking line 12. At its back end the catheter 9 is provided with an interlocking means 14 which serves to interlock the catheter 9 with the hollow needle 1 in axial direction by engaging with the attachment 4 of the hollow needle 1 in that way that the front end 10 of the catheter 9 which is positioned at the predetermined breaking line 12 aligns with the front end 7 of the hollow needle 1. In order to prevent rotation of the catheter 9 relative to the hollow needle 1 a protruding part or nose 15 of the interlocking means 14 is made to en-gage into an opening 16 formed at the attachment 4 of the hollow needle 1 for providing therewith a rotationally secure engagement.

The catheter 9 is made of, e.g., plastics and may have a tip or front end which consists of radiodense material for being detectable by X-rays. The length of the catheter may be in the order of, e.g., 20 cm.

Figure 6:
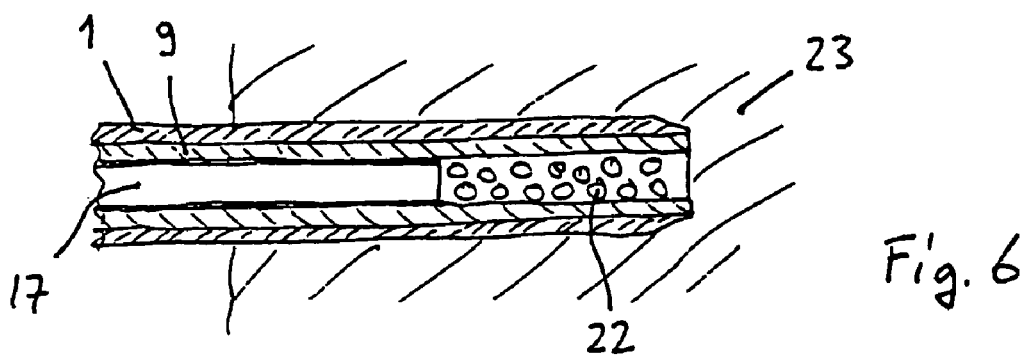
FIG. 6 is a lengthwise section through the hollow needle and the catheter inserted into the hollow needle and filled with capsules.

A long mandrin 17 (see FIG. 2) having a length of, e.g., 30 cm is insertable into the catheter 9 fitting therein with zero backlash and is axially slidable therein. The long mandrin 17 has marks 18 at its back section which assist in positioning the mandrin 17 in the catheter 9 in such a way that the mandrin 17 can easily be arranged in a first position in which its front end 19 coincides with the front end 10 of the catheter 9 having the sieve 11 removed, and in a second position in which the front end 19 of the mandrin 17 is pulled backwards, e.g., about 5 cm, so that a reservoir 20 of defined size is provided in the front section 21 of the catheter 9. The reservoir 20 is provided for receiving and holding, e.g., capsules 22 FIG. 6), which contain a medicament and which are to be delivered into a patient's body 23.

The mandrin 17 can be fixed relative to the catheter 9 by means of a mandrin stopper 24 in such a way that it is either securely fixed with the catheter 9 or at least hindered from being further inserted into the catheter 9. The mandrin stop-per 24 includes a locking element, e.g., a locking screw 25, which is held in the interlocking means 14 annularly surrounding the catheter 9 in a radially adjustable manner for clamping or fixing the mandrin 17 to the mandrin stopper 24. Alternatively, the mandrin stopper 24 constitutes an independent member, e.g., a ring which is slidably mounted on the mandrin 17 and can be fixed thereon so that by leaning against the back end of the catheter 9 the insertion movement of the mandrin 17 into the catheter 9 can be limited.

The injection device, arranged as shown in FIG. 1 with the cutting needle 2 inserted into the hollow needle 1 and interlocked therewith, is pushed forward with the cutting tip 3 cutting through the skin 26 and into the region of interest in a body 23, for example in a tumor, and the front end 7 of the hollow needle 1 will be positioned in the region of interest where the capsules 22 are to be delivered, e.g, with the aid of an ultrasonic or an X-ray apparatus which allows for checking the precise position of the injection device in the body. While keeping the hollow needle 1 in its position the cutting needle 2, after releasing the attachment 5 from the attachment 4 of the hollow needle 1, will be withdrawn from the hollow needle 1. The loaded catheter 9 containing the capsules 22 in its reservoir 20 and having the front section broken away which holds the sieve 11 will be inserted into the hollow needle 1 (FIG. 6) and will be pushed forward until both front ends coincide. Then the catheter 9 will be interlocked by means of the interlocking means 14 with the hollow needle 1. A short mandrin (e.g., 15 cm long) which is fully inserted within the catheter 9 while loading the catheter 9 is with capsules and which delimits the reservoir 20 is replaced by the long mandrin 17 which will be positioned at the catheter 9 in its rear position and borders the reservoir 20 filled with capsules 22.

Figure 7:
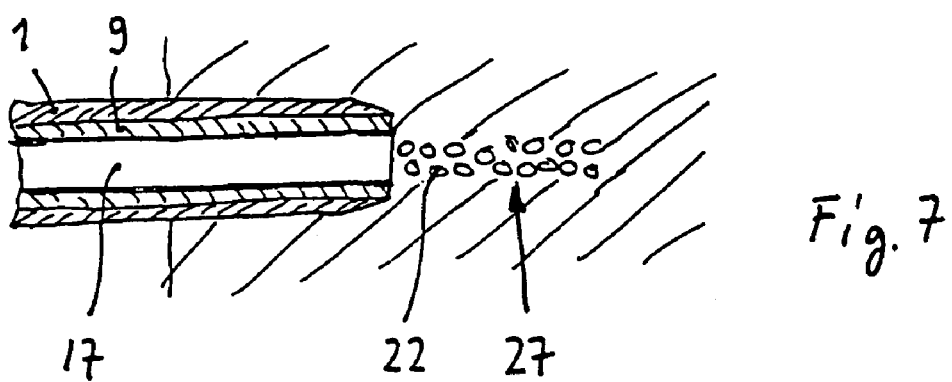
FIG. 7 is a lengthwise section through the injection device while the capsules are delivered.

Subsequently, the hollow needle 1 and the catheter 9 being interlocked by means 30 of the attachments 4 and 5 and with the mandrin stopper 24 being released from its interlocked position are withdrawn as a unit and are displaced relatively to the mandrin 17 which is held stationary relative to the body 23 FIG. 7).

Thus, while the hollow needle 1 and the catheter 9 are withdrawn, the capsules 22 contained in the reservoir 20 are released from their enclosure and are delivered into the insertion channel 27 in the body. In this way one can avoid that pressure will be exerted on the capsules 22 which pressure in case of injecting the capsules 22 by means of a syringe would act on the capsules 22 and might harm or destroy the elastic capsules 22. When the tip of the catheter 9 being withdrawn reaches the tip of the mandrin 17 (FIG. 7) the capsules 22 are completely set free in the insertion channel 27 formed in the body 23 and the hollow needle 1 together with the catheter 9 and the mandrin 17 are withdrawn from the body 23.

If another medicament is subsequently to be inserted into the body in the same location the catheter 9 together with the mandrin 17 are withdrawn from the hollow needle 1. However, the hollow needle 1 remains in the body 23 and will be pushed forward into its original position in the body before the next loaded catheter 9 will be inserted.

Subsequently, another catheter 9 which is filled with capsules 22 will be inserted into the hollow needle 1 and the capsules 22 are delivered, as described above, into the body by means of the injection device.

For loading or filling the catheter 9 capsules 22 are aspirated with a syringe from a sterile container. The syringe holding the capsules 22 is positioned at the reservoir 20 of the catheter 9 and the capsules are delivered into the catheter 9 by slowly pushing forward the piston of the syringe. By holding the catheter 9 vertical upright excess liquid can drop off through the sieve 11. The catheter 9 can be rinsed with a sterile saline until the dropping off liquid is clear. Then the short mandrin is inserted into the catheter 9 and interlocked with the catheter 9 in such a position that the reservoir 20 for the capsules at the front section of the catheter 9 is provided with a volume sufficiently sized to contain all capsules 22. The short mandrin will be replaced by the long mandrin 17 after the catheter 9 has been inserted into the hollow needle 1.

Figure 3:
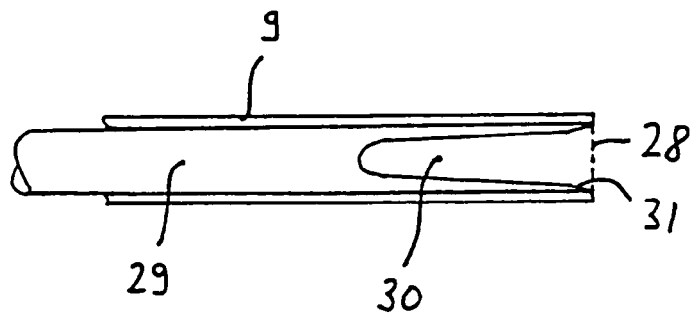
FIG. 3 is a lengthwise section through the catheter and the mandrin ac-cording to another embodiment.
Figure 4:
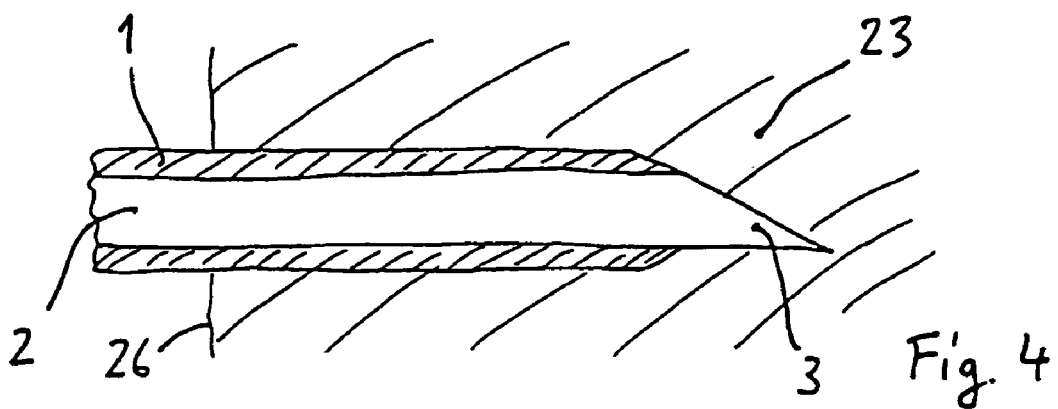
FIG. 4 is a lengthwise section through the front section of the injection de-vice while puncturing the body.
Figure 5:
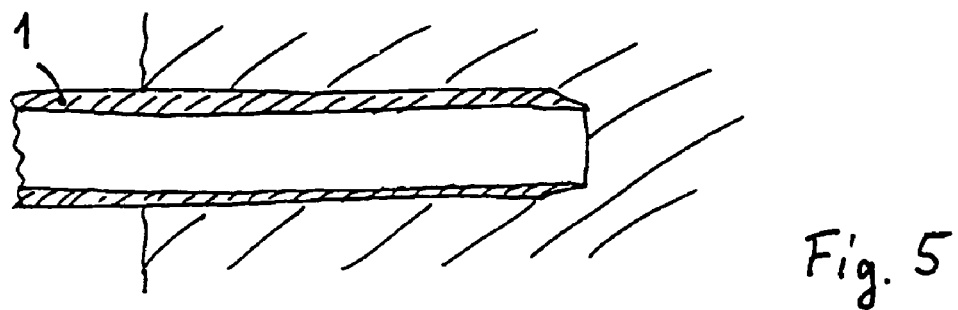
FIG. 5 is a lengthwise section through the hollow needle positioned in the body.

In an alternative embodiment of the invention the catheter 9 comprises at its front end a sieve 28 made of biologically degradable material (FIG. 3). The delivery mandrin 29 which is adapted to fit into the catheter 9 and to be pushed forward therein, includes a cavity as a reservoir 30 for the capsules 22 which is open to the front end and has a circular cutting edge 31 with a bevel edge inclined to the longitudinal axis. Apart from this the mandrin 29 corresponds to the mandrin 17. When the mandrin 29 is pushed into the catheter 9 which is filled with capsules 22 the capsules 22 move into the reservoir 30 while the mandrin 29 is advanced placing its cutting edge 31 next to the sieve 28 and is interlocked in this position (FIG. 8).

Figure 8:
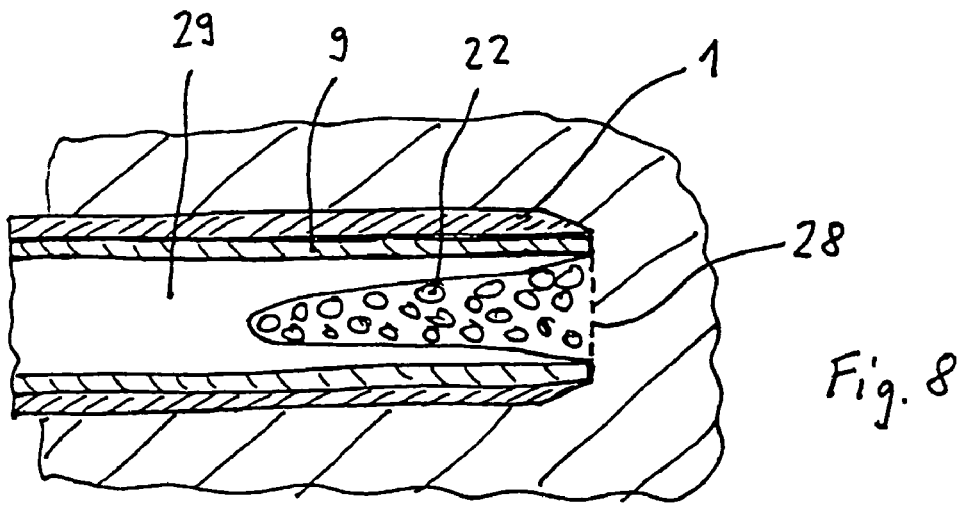
FIG. 8 is a lengthwise section through the hollow needle containing the catheter/mandrin arrangement according to the second embodiment.
Figure 9:
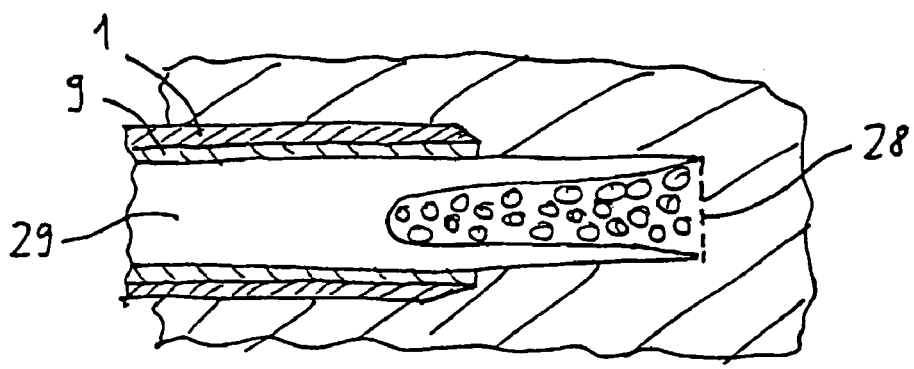
FIG. 9 is a lengthwise section through the arrangement of hollow needle and catheter which is retracted relative to the mandrin.
Figure 10:
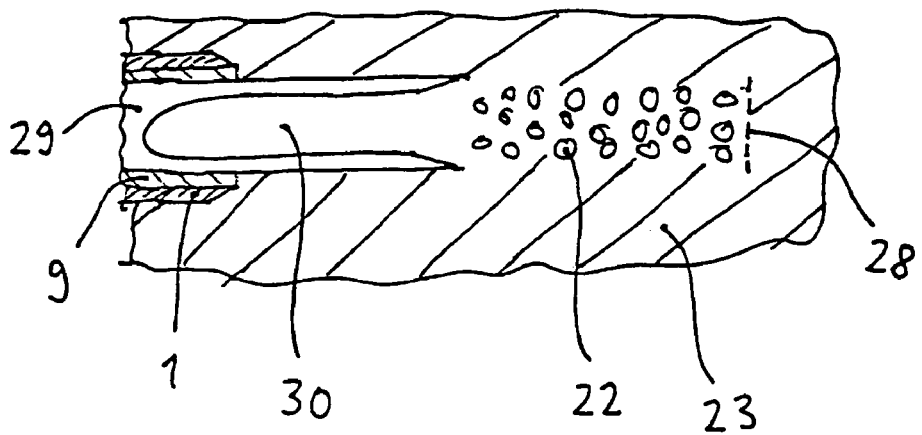
FIG. 10 is a lengthwise section through the injection device while being with-drawn from the body.

In order to deliver the capsules 22 the loaded catheter 9 is inserted into the hollow needle 1, according to the above description, which hollow needle 1 is positinned in the body 23 and advanced until the front ends of the catheter 9 and the hollow needle I coincide (FIG. 8). When the hollow needle 1 is withdrawn together with the catheter 9 being fixed to it the mandarin 29 being held stationary cuts the sieve 28 with the cutting edge 31 and separates it from the catheter 9 (FIG. 9) so that the reservoir 30 is open to the distal end and the capsules 22 can move or roll into the puncture channel 27 while the mandarin 29 is also withdrawn. The cross-sectional dimension of the reservoir 30 may decrease along the longitudinal axis from the open end to the interior and the reservoir 30 may be formed, e.g., with a longitudinal cross section in elliptical form, so that the capsules 22 can leave the reservoir 30 unhindered. The sieve 28 remains in the body 23 and degrades biologically.

The invention claimed is:

1. A method for introducing capsules containing a substance into a body by means of an injection device, comprising the steps of:

positioning a front or distal end of a hollow needle of the injection device in a target area in a body;

inserting a catheter in the hollow needle, the catheter having at its distal end a reservoir filled with capsules and a mandrin delimiting the reservoir;

withdrawing both the catheter and the hollow needle relative to the mandrin while the mandrin is held stationary whereby the capsules are delivered to the target area of the body without exerting any pressure;

afterwards withdrawing the mandrin from the body; and while the catheter is withdrawn relative to the mandrin cutting off a sieve, which is provided on the front end of the catheter and which delimits the reservoir distally, from the catheter by means of the mandrin.

2. The method defined in claim 1, wherein the catheter and the hollow needle are withdrawn from the mandrin while the mandrin is held stationary approximately over the length of the reservoir, after releasing the capsules, the catheter and the mandrin are completely withdrawn and the hollow needle is pushed forward in the target area for other capsules to be delivered, another catheter being filled with capsules and containing a mandrin will be pushed forward into the hollow needle, and again releasing the capsules in the body without exerting any pressure.

3. The method defined in claim 1, wherein the capsules are filled into the reservoir without exerting pressure, by means of a syringe.

4. Injection device comprising:

a hollow needle;

a cutting needle insertable in the hollow needle and slidable therein with a cutting tip protruding from a front or distal end of the hollow needle;

a catheter for replacing the cutting needle in the hollow needle, the catheter being slidable approximately up to the front end of the hollow needle and having at its distal end a reservoir for a substance in the form of capsules;

a mandrin which can be inserted into the catheter and which can be placed therein in a position in which it defines the reservoir filled with capsules on the distal end of the catheter, the capsules contained in the reservoir of the inserted catheter being released largely without exerting any pressure in the target area of a body once the injection device has been arranged in a target area of a body by relatively withdrawing both the catheter and the hollow needle in relation to the mandrin followed by withdrawal of the mandrin from the body; and a detachable sieve on a front end of the catheter delimiting the reservoir distally.

5. The injection device defined in claim 1 wherein a front end part of the catheter carrying the sieve is separable from the catheter at a predetermined breaking point.

6. The injection device defined in claim 1, wherein the mandrin is formed with an extension on its front section, said extension extending along the reservoir and comprising a cutting device for separating the sieve which remains in the body and which in particular is biologically degradable.

7. The injection device defined in claim 6, a cavity is located in the front part of the mandrin and is open to the front end of the mandrin and forms the reservoir, and the front end of the mandrin being made as a circular cutting edge.

8. The injection device defined in claim 7, wherein the cavity widens from an interior thereof in a direction toward the front opening.

9. The injection device defined in claim 1 wherein the mandrin can be arranged on the catheter in a first position in which the mandrin's front end is retracted from the front end of the catheter for delimiting the reservoir, and in a second position in which the front end of the mandrin is flush with the front end of the catheter (9).

10. The injection device defined in claim 1 wherein the mandrin has at least one mark providing a positioning help.

11. The injection device defined in claim 1 wherein a mandrin stopper is provided for optionally setting a limitation for the mandrin movement relative to the catheter.

12. The injection device defined in claim 1 wherein the catheter includes a radiodense section or a radiodense mark.

* * * * *